United States Patent [19]

Verschoor et al.

[11] Patent Number: 5,441,491
[45] Date of Patent: Aug. 15, 1995

[54] METHOD AND COMPOSITION FOR TREATING BIOPSY WOUNDS

[76] Inventors: Jacob Verschoor, 4847 CH Teteringen; Wiete Westerhof, Kanaalweg 23a, 1121 DP Landsmeer, both of Netherlands

[21] Appl. No.: 192,557

[22] Filed: Feb. 4, 1994

[51] Int. Cl.⁶ .............................................. A61F 13/00
[52] U.S. Cl. ....................................... 604/304; 602/43
[58] Field of Search ............................... 604/304–307; 206/440; 602/43

[56] References Cited

U.S. PATENT DOCUMENTS

| | | | |
|---|---|---|---|
| 4,407,787 | 10/1983 | Stemberger | 604/304 |
| 4,909,243 | 3/1990 | Frank et al. | 604/304 |
| 5,067,961 | 11/1991 | Kelman et al. | 623/5 |
| 5,123,900 | 6/1992 | Wick | 602/43 |

FOREIGN PATENT DOCUMENTS

0182842B1 3/1993 European Pat. Off.

*Primary Examiner*—Jerome L. Kruter
*Attorney, Agent, or Firm*—Zarley, McKee, Thomte, Voorhees & Sease

[57] ABSTRACT

A method and composition for treating biopsy wounds in human patients is provided. The process involves filling the wound with a disc of collagenous material coated with elastine, with the disc of material being of a size to substantially fill the biopsy wound. The collagenous material is preferably derived from the skin of hoofed animals such as calves, sheep and pigs. The disc is combined with a microporous top layer, preferably polyether urethane.

This combination is easy to apply and leads to hemostasis, improved wound healing and less wound contraction and scarring.

17 Claims, 1 Drawing Sheet

METHOD AND COMPOSITION FOR TREATING BIOPSY WOUNDS

BACKGROUND OF THE INVENTION

Punch biopsies are commonly taken by doctors during a variety of medical test procedures. This is especially true for dermatologists who commonly take punch biopsies for diagnostic purposes in numerous skin condition evaluations. The usual procedure after taking a punch biopsy involves pressing the patient's wound with a gauze for five to ten minutes, suturing of the wound, and applying a gelatin sponge cube under an adhesive tape. This process is not very satisfactory. For example, continual pressing treatment of the wound for even a five to ten minute period involves expensive time of a dermatologist or nurse, to say nothing of the patient's time. Moreover, suturing of the wound involves usage of sterile instruments and sterile disposables which are quite expensive. Suturing also may result in a scar. Finally, the application of a gelatin sponge cube under an adhesive tape is often not effective in stopping the bleeding, i.e., when the sponge is blood soaked it starts to leak.

It can therefore be seen that even with the present state of the art there is a substantial need for an efficient way of achieving hemostasis with biopsy wounds. Moreover, there is a continuing need for a way of treating biopsy wounds which not only controls bleeding but also improves wound healing with limitation of scar formation.

It is a primary objective of the present invention to provide both an effective method and an effective treatment composition for biopsy wounds.

Another objective of the present invention is to provide a method of treatment and a composition which not only provides hemostasis, but also improves wound healing with limitation of scar formation.

An even further objective of the present invention is to provide a method of treatment of biopsy wounds which avoids the need for suturing of the wound.

The method and manner of accomplishing each of the above objectives as well as others will become apparent from the detailed description of the invention which follows hereinafter.

BRIEF DESCRIPTION OF THE INVENTION

SUMMARY OF THE INVENTION

Figure 1:
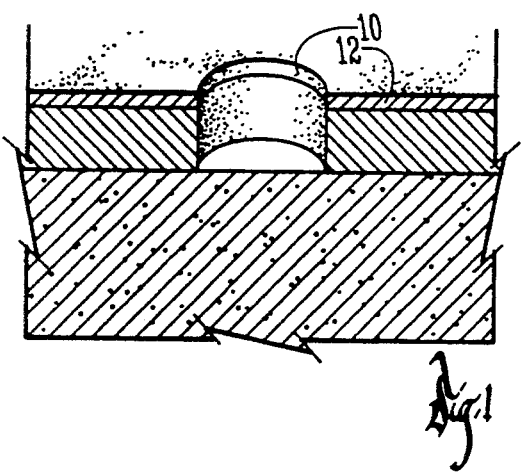
FIG. 1 is a sectional view through a biopsy punch of the epidermal skin layer.

Biopsy wounds are treated with collagen discs that are essentially of the same dimension as the biopsy wound. The discs are preferably combined with a microporous top layer, for example made of polyether urethane. The disc is a collagenous material that is preferably coated with elastine at a level of 1%–20% by weight of the collagen and most preferably at a level of 1% to 5% of elastine by weight of the collagen material. The microporous top layer preferably has a pore size of 0.3 to 1.0 microns. The top layer may be shaped in the form of a disc overlapping the collagen disc and combined with an adhesive material in order to fixate the combination in the wound bed.

DETAILED DESCRIPTION OF THE INVENTION

Wound healing has several distinct phases: inflammation: platelet aggregation, cell recruitment; granulation tissue formation: neovascularization; and extracellular matrix deposition: wound contraction. Components of the extracellular matrix, including collagens, are involved in every stage of wound healing. The first event, immediately following injury, is blood vessel disruption leading to extravasation of blood constituents, followed by platelet aggregation and blood coagulation. Collagens have a key role in these processes. Exposed collagens in the wound promote platelet aggregation following vascular injury. Aggregating platelets release a large number of cytokines including platelet-derived growth factor (PDGF), a potent mitogen, and transforming growth factor Beta (TGF Beta), a potent stimulator of extracellular matrix synthesis.

Platelets also release a number of other molecules including fibrin, fibronectin and thrombospondin which further blood coagulation and are chemotactic for inflammatory cells. Neutrophils, the first cells recruited into the wound site, are responsible for removing bacteria from the area by releasing a large arsenal of proteolytic enzymes. Many of these enzymes are also capable of degrading components of the extracellular matrix.

Collagen is frequently described as a stable, relatively inert component of the extracellular matrix. While this statement may be true of the collagens deposited and crosslinked into an extracellular matrix, the primary role of which is to provide an extracellular framework or scaffold to support cells, collagens have been increasingly considered to be dynamic proteins involved in many cellular and developmental processes. Distinct roles have been elucidated for collagens during morphogenesis and development, platelet adhesion and aggregation, cell attachment, cell migration, angiogenesis and filtration in basement membranes.

Contemporary techniques to assess collagen turnover have also indicated that collagen metabolism is much more rapid than once considered.

While collagens have been used in the past for skin grafts and for permanent repair for cutaneous wounds and soft tissue injuries, collagen, preferably native, non-reconstituted collagen coated with elastine has not been previously transformed into discs or plugs or used for biopsy plugs in the manner described herein.

The collagen discs for use in the present invention are made of collagen derived from young, fresh skin of calves. While calf skin is preferred, it may also be possible to use the skin of other animals such as young pigs. The collagen is preferably coated with elastine at a level of from 1% to 20% by weight of the collagenous material, preferably 1% to 5%, and most preferably at a level of from 1% to 3% elastine by weight of the collagen material. Preferably the collagen material is one from which non-fibrous tissue proteins and glycoproteins as well as lipids and lipid residues have been removed, with the collagen being chemically crosslinked. It is also preferred that the collagen is treated to remove telopeptides responsible for allergic reaction.

The collagen obtained above maintains its hemostatic potency and achieves hemostasis in less than four minutes in 86% of the cases. It is biocompatible and when left in situ is gradually absorbed.

The collagen trabeculae are coated with elastine which stimulates cell proliferation and migration, while the collagen fiber structure is maintained. This is a characteristic of a mature dermal architecture.

The collagen in elastine coated form retains the hemostatic activity of the native collagen. They can be applied directly to a bleeding biopsy wound without the chance of dispersion of blood over outer skin. They act as supporting framework for the aggregation of platelets and subsequent stable fibron clot formation.

It has been shown that collagenous material coated with elastine in combination with a microporous polyether urethane top layer did lead to improved wound healing with limitation of scar formation. This is a significant benefit since polyether urethane sponges/sheets normally give rise to severe foreign body reaction and consequent scar formation when used as a template for wound repair.

Likewise, collagen alone has been used in the past to enhance wound healing; however, it frequently leads to inflammation, rejection, drying out of the wound and scar formation. The combination of collagen coated with elastine and combined with a microporous polyether urethane top layer showed significantly reduced scar formation and also improved wound healing, thus giving benefits not achievable by either collagen alone or polyether urethane sponges.

The combination gives rise to a balanced migration and proliferation of fibroblasts with a significant decrease in the expression of myofibroblasts and consequently better random organization of collagen fibers as seen in normal dermis. This gives rise to less contraction, less scarring and better functional and cosmetic results.

In normal dermis elastin is present in the form of fibers; however, in the collagen sheets used in the invention, the fibers are coated with elastin, preferably the alpha hydrolysate form of elastin (CfN-Herstellung von Naturextracten CmbII, Michelbach, Germany), by for example dipping and soaking the collagen sheet into a water solution of elastin. The concentration should be at least 1%; it is held at ambient temperature in the solution for preferably at least 5 minutes. The elastin coating of the fibers may be checked with immunohistochemistry using the anti-elastin monoclonal (for example mouse IgG1 anti-bovine alfa elastin, clone BA-4, Sigma, St. Louis, Mo., USA). Alternatively, spraying or printing techniques may be used to coat the fibers with elastin.

The initial processed material is in sheets but in accordance with the process of the present invention are preferably punched into discs of substantially the same size as the biopsy wound. The discs can be individually packaged in a peel strip with the film cover of the peel strip peeled back to reveal one plug at a time without making the other discs unsterile. Alternatively, any type of sterile package can be used.

Figure 3:
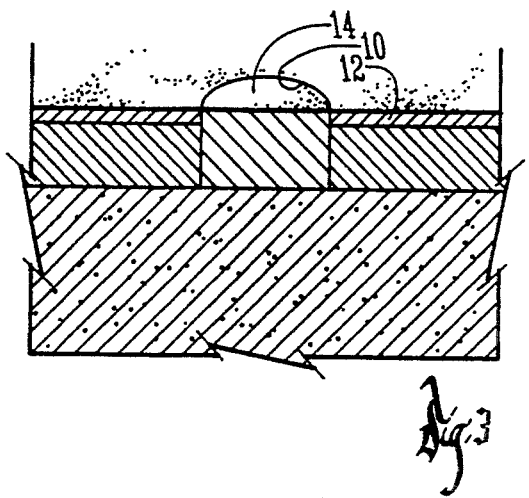
FIG. 3 is a sectional view as shown in FIG. 1 but with the biopsy punch filled with a collagen disc.
Figure 2:
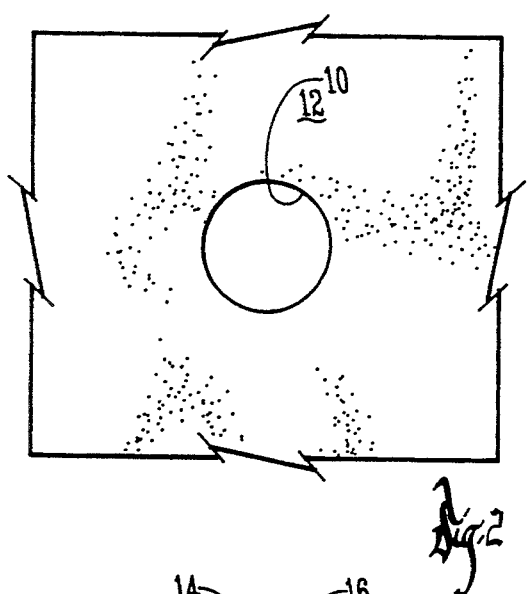
FIG. 2 is a plan view of the biopsy punch of FIG. 1.
Figure 4:
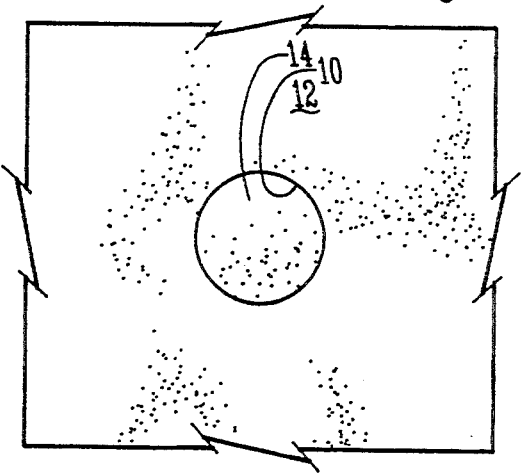
FIG. 4 is a plan view of the filled biopsy punch.
Figure 5:
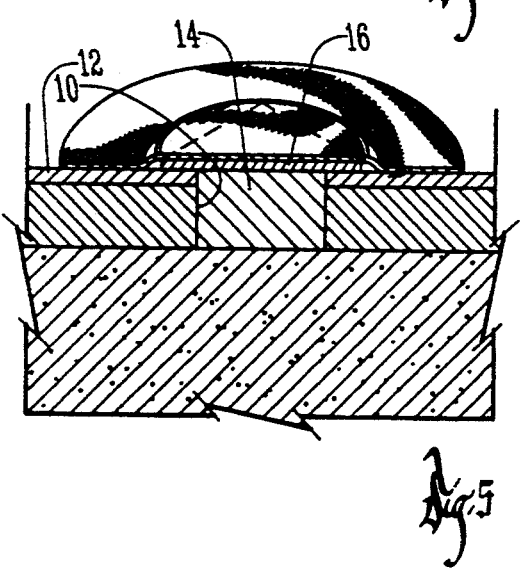
FIG. 5 is a sectional view of the filled biopsy punch with a covering bandage.
Figure 6:
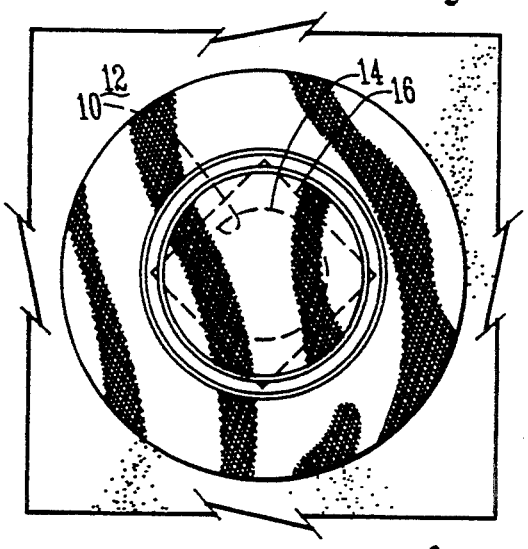

FIG. 1 shows a biopsy punch 10, through the epidermis 12. As shown in FIG. 3, the collagen with elastine disc 14 of mating dimension to the biopsy punch 10 is inserted into the biopsy punch 10 and covered with a microporous polyether top layer 16. This will promote improved wound healing with limited scar formation.

Next to the individually packed collagen discs, polyether urethane discs with an adhesive material will be added. The adhesive material is needed to fixate the combination into the wound bed.

EXAMPLES

The following examples are offered to demonstrate results of a clinical trial conducted at one medical center with the collagen discs in combination with a microporous polyether urethane top layer.

Full thickness skin defects tend to heal with wound contraction and scar formation. When a full thickness skin defect comprises a large area, as is often the case with burns, wound contraction can be impressive and give rise to disabling contractures. The cosmetic appearance of scars often leads to great discomfort and mental distress. These phenomena arise because dermal regeneration is defective. The normal dermal architecture, with random organization of collagen bundles and a fine extensive elastin fiber network contributes to skin characteristics like strength, elasticity and flexibility. In contrast, scar tissue shows an aberrant architecture with large parallel organized collagen bundles and a scattered elastin fiber network, which explains the rigid and stiff features of scar. These unwanted processes can be controlled by stimulating dermal regeneration. With a recently developed technique based on scattering of laser light, scarring can not be quantified. In these examples the laser technique was used to evaluate the contribution to dermal regeneration of collagenous substitutes with different extracellular matrix proteins. The results below show the superiority of the combination of this invention.

Native collagen, build up from insoluble collagen fibers, remained intact for a longer period (up to two weeks). Addition of extracellular matrix proteins like elastin made the native collagen matrices even more resistant to biodegradation. These dermal substitutes remained intact up to four weeks without eliciting any foreign body reaction. The fibrillar structure of the elastin coated native collagen matrices functioned sufficiently long as a scaffold for migration and proliferation of cells and stimulated the formation of mature collagen fibers.

In the clinic tests under normal procedure persistent venous leg ulcers are grafted with autologous full thickness punch biopsies. The biopsies are taken from the upper thigh and transferred to the ulcer. The arising donor side wounds provide an excellent tool to study dermal repair in a human wound model. Without any extra discomfort to the patient, identical wounds receiving different kinds of treatments can be and were evaluated. The multiple wounds can be classified as full thickness skin defects of controlled depth. In the tests here described implanted native non cross-linked collagen templates with different extracellular matrix proteins were placed into the punch biopsy holes. Since all wounds are of the same size and depth, intra-patient evaluation is allowed.

Seven patients admitted to the clinic for a persistent venous ulcer larger than 10 cm × 10 cm were included in this study. Leg ulcers based on arterial insufficiency were excluded. The age of patients ranged between 65 and 95 years (total number=13, mean=77.8, standard deviation=9.1). They did not suffer from any systemic disease which might interfere with wound healing like: diabetes mellitus, auto-immunological disorders, immune deficiencies. The patients did not use immunodepressants.

The upper thigh served as donor side. The skin area was shaved, and subsequently disinfected. The donor side area was anesthetized locally with subcutaneous injections of lidocain 0.5% with adrenaline 20 mg/ml. Fifty 6 mm punch biopsy holes were created and divided in five groups of 10 wounds. One group served as control and was left untreated. The other four groups were treated with dermal matrices.

Collagen discs made of large insoluble native collagen type I fibers of bovine origin, 2 mm thickness and 6 mm in diameter were prepared. Before application, the collagen substitutes were linked with: (1) α-elastin hydrolysate in a concentration of 3 w/w %; (2) fibronectin in a concentration of 0.1 w/w %; (3) hyaluronic acid in a concentration of 0.1 w/w %; or (4) left without additions. Characterization of the used components are listed in Table 1 and the results in Table 2 and Table 3. All wounds were covered with a microporous (0.3 microns) polyether urethane membrane. This membrane prevented bacterial contamination.

In all patients wounds were epithelialized after 7 days, and the collagen matrices were incorporated in the wound tissue underneath the epithelium. At 2 weeks the polyurethane cover detached spontaneously together with the wound crust. Wound infection occurred in one patient, probably caused by manipulation of the protective bandage. This patient was excluded from further evaluation.

Wound contraction showed large inter-patient variation, but intra-patient results were consistent. For this reason the paired t-test was used to detect statistically significant differences. After 6 weeks, control wounds without dermal substitution showed most wound contraction. The diameter of these defects was 20±4% smaller than the initial wound diameter. Less wound contraction was noticed in wounds treated with native collagen without additional extracellular matrix proteins (15±5% diameter reduction). Addition of extracellular matrix proteins to the collagen sponges had little extra reducing effect on wound contraction at week 6 (hyaluronic acid addition 14±6% diameter reduction, fibronectin addition 14±5% and elastin addition 16±4%). Significant differences were noticed between control wounds and fibronectin treated wounds ($p<0.02$, mean difference 2.8 mm±standard error of the differences 0.8) and between control wounds and elastin treated wounds ($p<0.02$, mean difference 2.4 mm±standard error of the differences 0.8).

Six weeks after implantation no collagen fibers from the dermal matrix could be detected. In the regenerating tissue of hyaluronic acid and fibronectin treated wounds, few lymphocytes were present. In all wounds newly formed dermal tissue with typical aspects like an abundant amount of cells, a dense capillary bed and immature collagen bundles were present. In sirius red stained sections small mature bundles were noticed. The regenerated collagen bundles in the control wounds were organized parallel to the epidermis where in the elastin treated wounds a more random organization was observed.

After 3 months no elastin regeneration could be detected with the anti-elastin monoclonal. A sharp demarcation between old tissue containing elastin and new tissue without elastin was visible in all wounds. The collagen with elastin product produced superior skin reparation without scar tissue in all cases. At that time, no lymphocyte infiltrates could be found in any of the wounds. In elastin and fibronectin treated wounds regenerated epidermis showed rete ridges. Wounds that received native collagen without additions or hyaluronic acid were covered with thin flat epidermis. The elastin containing collagen discs were superior in all respects in promoting wound healing without scar tissue formation. The fibronectin tends to cyst formation rather than thin epithelial tissue.

TABLE 1

CHARACTERISTICS OF DERMAL MATRICES

| Matrix composition | Number of Tests | Pore size | Disintegration Speed |
|---|---|---|---|
| Native Bovine Collagen type 1 from bovine tendons (NBC) | 6 | 75 um | 2 weeks |
| NBC + 3 w/w % α-elastin hydrolysate from bovine ligamentum nuchae (of which 4/5 parts MW ± 60 kD and 1/5 part MW ± 200 Kd) | 6 | 75 um | 4 weeks |
| NBC + 0.1 w/w % fibronectin from bovine plasma (440 Kd) | 6 | 50 um | 4 weeks |
| NBC + 0.1 w/w% hyaluronic acid from bacteria (MW between 700 Kd and 1500 Kd) | 6 | 50 um | 4 weeks | a) Disintegration speed was assessed in a porcine skin wound model as described in Wound Repair and regeneration vol. 1 number.. pp... ....., 1994)

TABLE 2

WOUND CONTRACTION

| Treatment Modality | Contraction ratio ± standard error of the mean (in %) | Mean difference ± standard error of the difference (versus control, in mm) | Paired t-test result (versus control) |
|---|---|---|---|
| Control | 20 ± 4 | n.a. | n.a. |
| Native collagen no additions | 15 ± 5 | 2.2 ± 1.2 | 0.12 |
| Native collagen plus hyaluronic acid | 14 ± 6 | 3.2 ± 1.3 | 0.06 |
| Native collagen plus fibronectin | 14 ± 5 | 2.8 ± 0.8 | 0.02 |
| Native collagen plus elastin | 16 ± 4 | 2.4 ± 0.8 | 0.02 |

TABLE 3

ORIENTATION RATIO
(QUALITY OF NEW-FORMED SKIN)

| Treatment modality | Orientation Ratio ± Standard Error of the Mean (in %) | Unpaired t-test Results (Versus Control) |
|---|---|---|
| Normal skin | 1.36 ± 0.09 | <0.00001 |
| Control | 2.23 ± 0.06 | n.a |
| Native collagen no additions | 2.12 ± 0.28 | 0.73 |
| Native collagen plus hyaluronic acid | 1.81 ± 0.25 | 0.18 |
| Native collagen plus fibronectin | 1.78 ± 0.21 | 0.10 |
| Native collagen plus elastin | 1.33 ± 0.09 | 0.0002 |

In summary, Tables 2 and 3 illustrate the following: Table 2 shows wound contraction for the composition of the invention and for fibronectin was significant and about the same; however, Table 3 shows with the composition of the invention the collagen formation was random fiber (1.33) equal to normal skin whereas with fibronectin with substantially more parallel orientation resulting in far more likely scar formation.

It therefore can be seen that the invention accomplishes at least all of its stated objectives.

What is claimed is:

1. A method of treating a biopsy wound in a human patient comprising:
   filling said wound with a disc of fibrous collagenous tissue material from which non-fibrous tissue proteins and glycoproteins as well as lipids and lipid residues have been removed and which has been crosslinked chemically.

2. The method of claim 1 wherein the collagenous material contains from about 1% to about 20 wt. % of elastine, based on the collagenous material.

3. The method of claim 1 wherein the collagenous material contains from about 1% to about 5% by weight of elastine, based on the collagenous material.

4. The method of claim 1 wherein said disc is first punched from a sheet of collagenous material with the aid of a same-dimension needle which has been used for taking the biopsy punch in creating the biopsy wound.

5. The method of claim 1 wherein the exterior surface of the disc opposite the wound contact side is covered with a porous membrane to prevent microorganisms from infecting the wound.

6. The method of claim 1 wherein the disc of collagen material is derived from the skin of calves not older than six months.

7. The method of claim 6 wherein substantially all of the telopeptides responsible for the antigenicity of collagen are removed by mild chemical treatment.

8. The method of claim 6 wherein the collagen discs achieve hemostasis in less than 4 minutes.

9. Discs for treating biopsy wounds comprised of:
   collagenous material of which the collagen fibers are coated with alpha hydrolysate elastine.

10. The discs of claim 9 which centain from about 1% to about 5% by weight of elastine based on the collagenous material.

11. The discs of claim 10 which contain from about 1% by weight to about 3% by weight of elastine based on the collagenous material.

12. Packaged collagen discs comprising:
   a plurality of discs for treating biopsy wounds, each of said discs being comprised of a collagenous material coated with alpha hydrolysate form of elastine, said plurality of discs having a microporous top layer and packaged in a sterile way.

13. The packaged discs of claim 12 wherein said discs are combined with a 0.3 to 1.0 micron microporous top layer.

14. The packaged discs of claim 13 wherein the microporous top layer is a membrane made of polyether urethane.

15. The packaged discs of claim 14 wherein the discs contain from about 1% by weight to about 5% by weight of elastine.

16. The packaged discs of claim 15 wherein the top layer membrane is shaped in the form of a disc, overlapping the collagen disc with at least one millimeter.

17. The packaged discs of claim 16 wherein the discs are combined with an adhesive material in order to fixate the combination into the wound bed.

* * * * *